United States Patent [19]

Kewley et al.

[11] Patent Number: 5,582,797

[45] Date of Patent: Dec. 10, 1996

[54] SENSOR SUPPORT SUBASSEMBLY

[75] Inventors: Eric L. Kewley, Alameda; Joseph D. Bisby, Fairfield, both of Calif.

[73] Assignee: Andros Incorporated, Berkeley, Calif.

[21] Appl. No.: 396,931

[22] Filed: Mar. 1, 1995

[51] Int. Cl.[6] ............................. G01N 27/00; G01N 27/26
[52] U.S. Cl. ........................... 422/83; 422/90; 422/94; 422/98; 204/400; 204/409; 73/23.2; 73/31.05
[58] Field of Search ......................... 422/83, 90, 94–98; 73/23.2, 31.05, 31.06; 204/415, 153.1, 153.17, 400, 409, 153.18

[56] References Cited

U.S. PATENT DOCUMENTS

| | | | |
|---|---|---|---|
| 3,768,259 | 10/1973 | Caranahan et al. | 60/276 |
| 4,096,050 | 6/1978 | Kobayashi et al. | 204/428 |
| 4,098,653 | 7/1978 | Kita et al. | 204/153.18 |
| 4,193,965 | 3/1980 | Cullingford et al. | 422/98 X |
| 4,481,804 | 11/1984 | Eberhard et al. | 204/400 X |
| 4,551,801 | 11/1985 | Sokol | 364/424 |
| 4,569,748 | 2/1986 | Yamakawa et al. | 204/429 |
| 4,736,617 | 4/1988 | Hühmer et al. | 73/23.2 |
| 4,833,882 | 5/1989 | Yasuda et al. | 60/276 |
| 4,869,874 | 9/1989 | Falat | 422/53 |
| 5,017,340 | 5/1991 | Pribat et al. | 422/98 |
| 5,055,270 | 10/1991 | Consadori et al. | 422/98 |
| 5,316,647 | 5/1994 | Martell et al. | 204/415 |

FOREIGN PATENT DOCUMENTS

| | | | |
|---|---|---|---|
| 166408 | 1/1986 | European Pat. Off. | 422/98 |
| 6-160338 | 6/1994 | Japan . | |
| 698456 | 10/1953 | United Kingdom | 422/98 |

*Primary Examiner*—Arlen Soderquist
*Attorney, Agent, or Firm*—Coudert Brothers

[57] ABSTRACT

An improved sensor support subassembly for a chemical sensor in the testing of gaseous emissions. The sensor support subassembly of the present invention comprises means for slideably engaging a sensor unit with a gas intake manifold block. The sensor unit comprises a cylindrical base which forms the inlet to the sensor. The manifold block comprises a gas intake means, a gas channel and a U-shaped slot for slideably engaging the sensor unit's cylindrical base within the manifold block such that an air-tight passage is formed between the sensor inlet and the gas channel. The sensor support subassembly also provides a sealing means for ensuring an air-tight seal between the sensor unit and the manifold block. This slidable engagement scheme allows the sensor unit to be rotated about the axis of the cylindrical base, which in turn facilitates the use of a card-edge connector for making the electronic connections between the sensor and the sensor testing system power and data lines.

2 Claims, 2 Drawing Sheets

U.S. Patent    Dec. 10, 1996    Sheet 1 of 2    5,582,797
FIG._1
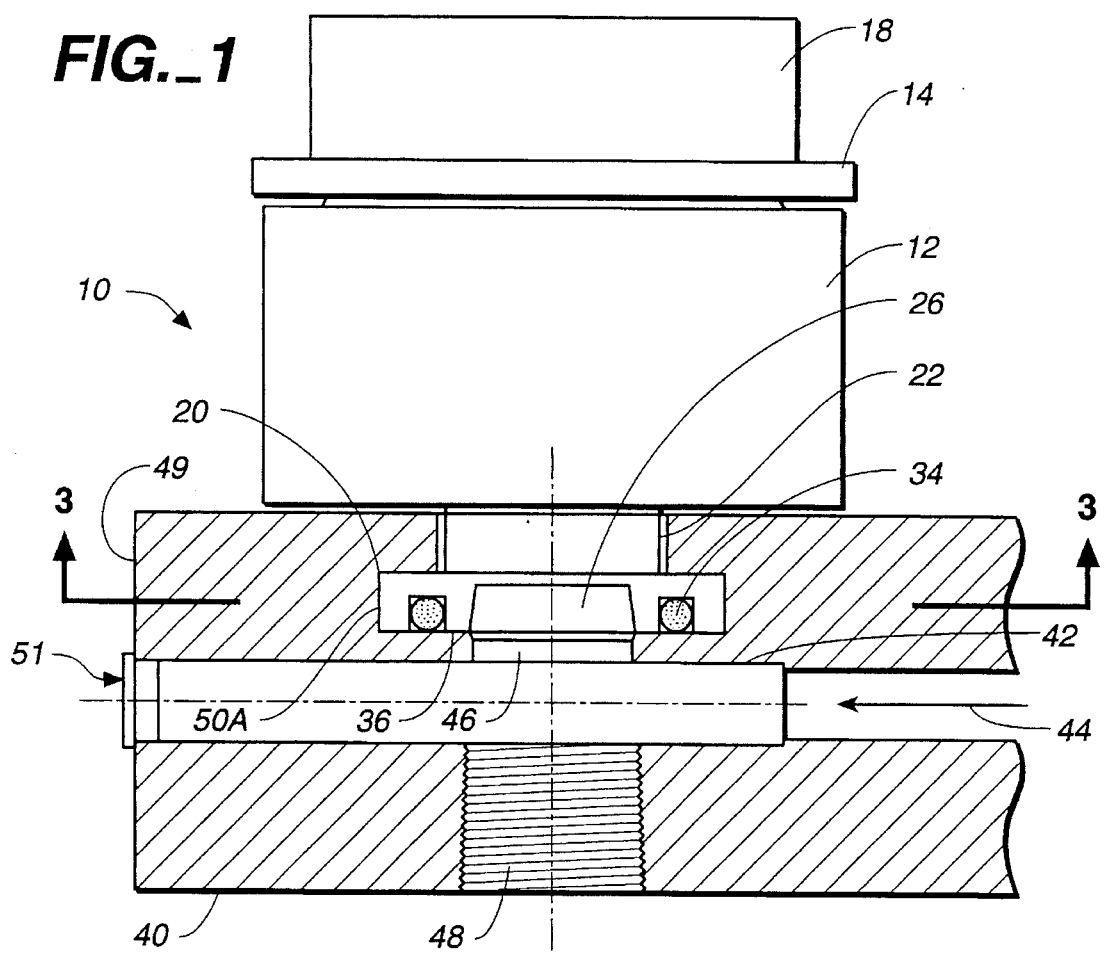
FIG._3
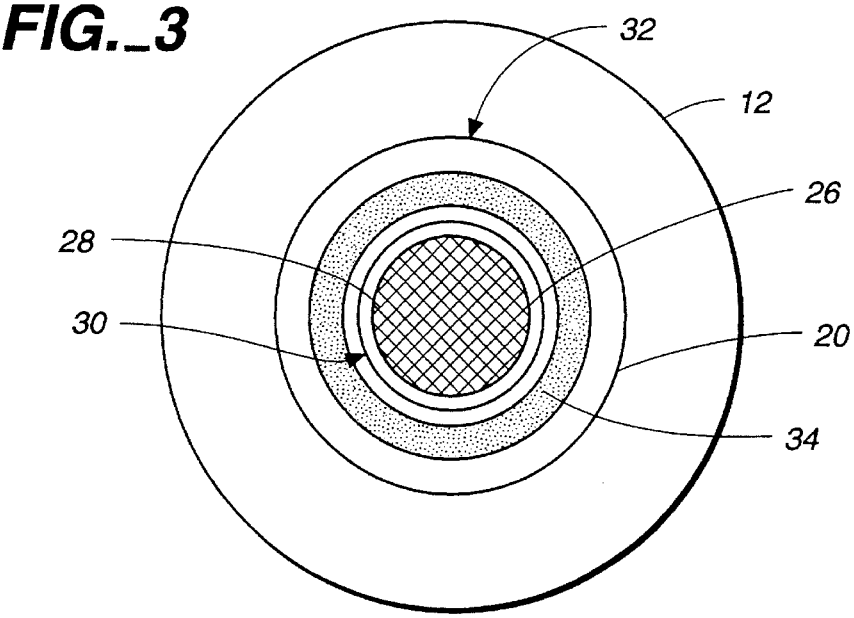

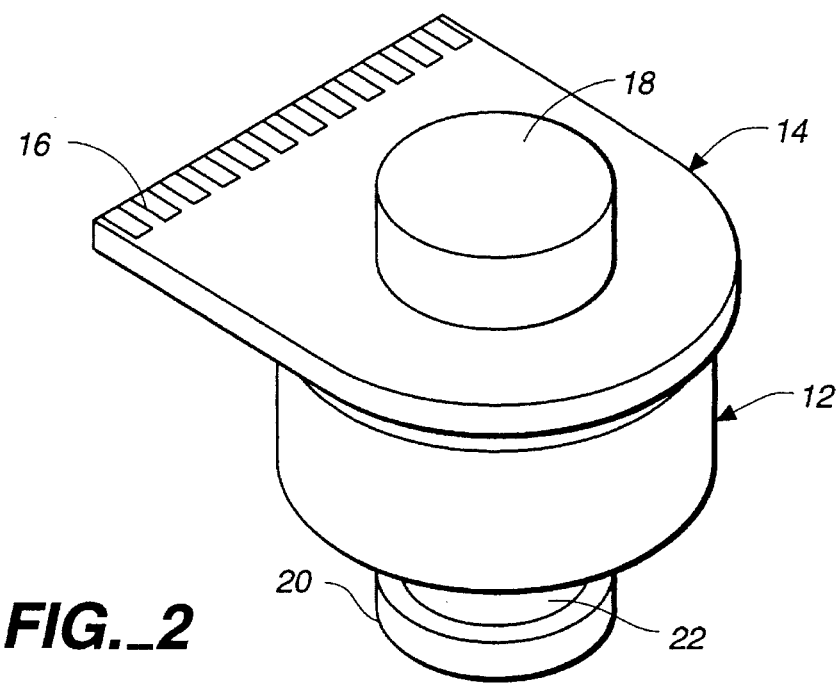
FIG._2
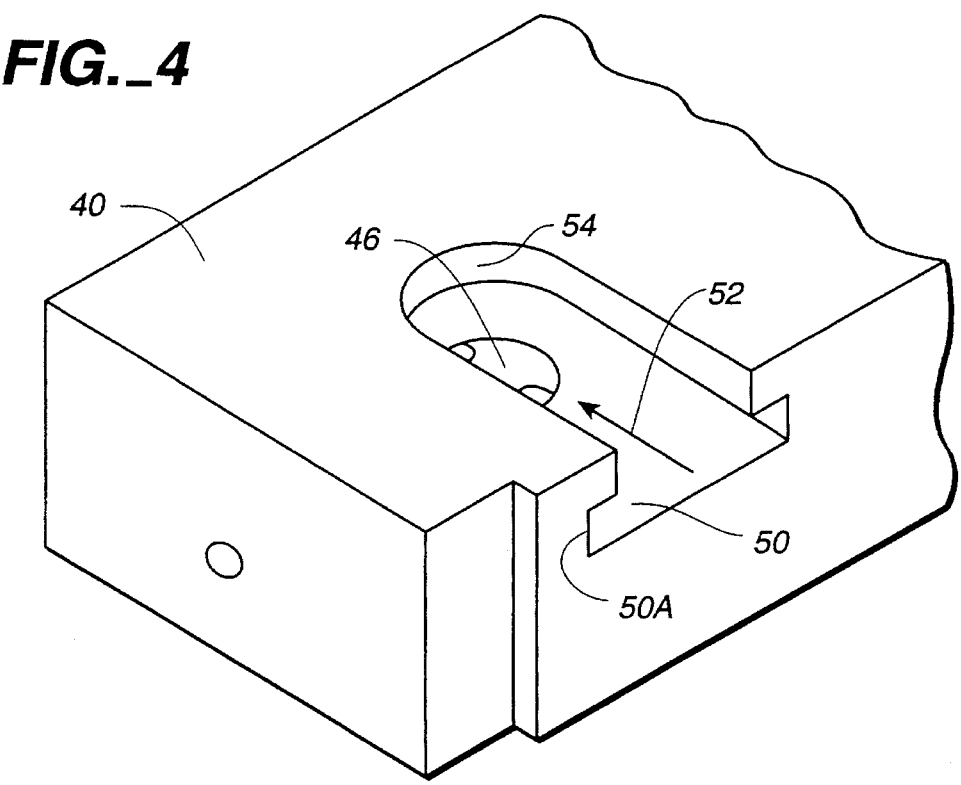
FIG._4

SENSOR SUPPORT SUBASSEMBLY

FIELD OF THE INVENTION

The present invention relates generally to chemical sensors, and more particularly to an improved sensor support subassembly for use with a chemical sensor which employs a card-edge connector.

BACKGROUND OF THE INVENTION

Chemical sensors are widely used in environmental and automotive applications for the monitoring and detection of hazardous or pollutant emissions, such as freon, ammonia and automobile exhaust gases. For example, chemical sensors are employed in the automotive service industry to monitor the performance of an automobile's exhaust gas recirculation (EGR) valve, a process commonly known as a "smog check." The EGR valve controls the emission of carbon monoxide, carbon dioxide, hydrocarbons released from unburned fuel, oxygen, as an indicator of a fuel system's air consumption, nitric oxide and other gases.

A typical system for testing exhaust emissions employs sensors that screw into the gas intake or manifold block. There are several disadvantages of a threaded sensor-manifold mating protocol. First, a threaded-screw connection limits the type of electronic interface that can be made with such a sensor. There are multiple electrical connections that are required between the sensor and the sensor circuitry (on a PC board) and between the circuitry and system inputs (e.g., power, ground, etc.) and outputs (e.g., digital display, etc.). Because of the need for multiple connections, a card-edge connector would be ideal. However, because a threaded mating scheme has inconsistent and unpredictable fitting tolerances, depending on the amount of torque applied, a card-edge connector is not practical. Instead, these multiple electrical connections are possible only with a "crimp and poke" connector, such as manufactured by Molex. These type of connectors are relatively bulky and are consequently subject to repeated bending and flexing. Repetitious flexing of wire can result in unreliable electrical contacts and therefore unreliable sensor performance.

Another disadvantage of prior art gas sensor-manifold connections, is the unreliability of the seal between the two. Of course, the more air-tight the seal, the more accurate the sensor measurement. Screw-in sensors are not fully air-tight if not correctly seated. Even with the use of a washer or o-ring seal, the results are dependent upon the tightness of the screw connection and the size of the washer employed.

Accordingly, it is a general object of the present invention to provide an improved sensor support subassembly.

Another object of the present invention is to provide a sensor support subassembly having a more flexible and reliable means of coupling the sensor to the gas manifold.

Another object of the present invention is to provide a sensor support subassembly having a highly reliable electrical connection scheme that improves upon the prior art.

Another object of the present invention is to provide a sensor support subassembly with an improved air-tight seal between the sensor and manifold block.

SUMMARY OF THE INVENTION

These and other objects of the invention are achieved by a sensor support subassembly which comprises a sensor unit having gas inlet means, a manifold block having a gas channel, and means for slideably engaging the sensor unit with the manifold block such that an air-tight seal is created between the gas inlet means and the gas channel. The means for slideably engaging comprises sensor unit mating means and manifold block mating means wherein the manifold block mating means slideably receives the sensor unit mating means. Specifically, the sensor unit mating means comprises a cylindrical base, extending from the sensor unit, which forms the gas inlet means, and the manifold block mating means comprises a U-shaped slot having dimensions corresponding to those of the cylindrical base such that said cylindrical base is frictionally engageable within the manifold block. Additionally, the cylindrical base is rotatable about its axis when engaged within the U-shaped slot. To further ensure an air-tight seal between the gas inlet means and the gas channel, the cylindrical base has a compressible ring inlaid on a surface which is to be frictionally engaged within the manifold block.

BRIEF DESCRIPTION OF THE DRAWINGS

Further features and advantages of the present invention will become apparent from the following, more particular description of the preferred embodiment of the invention, as illustrated in the accompanying drawings, in which like reference numbers generally refer to the same parts or elements throughout the drawings, and in which:

FIG. 1 is a cross-sectional view of a sensor support subassembly in accordance with the present invention.

FIG. 2 is a perspective view of a sensor assembly in accordance with the present invention.

FIG. 3 is a bottom view of the sensor assembly of FIG. 2.

FIG. 4 is a perspective view of a manifold block in accordance with the present invention.

DETAILED DESCRIPTION OF THE PREFERRED EMBODIMENT

Referring now to the drawings, there is shown in FIG. 1 a cross-sectional view of a sensor support subassembly 10 of the present invention for use, for example, in a sensor system tester for testing the performance of an automobile's emissions system. Sensor support subassembly has a sensor 12 which is slideably mated with manifold block 40.

FIG. 2 illustrates sensor 12 and its accompanying components. Mounted on top of and electronically coupled to sensor 12 is printed circuit (PC) board 14 having a card-edge connector 16. PC board 14 provides sensor 12 access to the tester system power and data lines 16 via a PC board plug (not illustrated) which couples with card edge connector 16. Mounted on top of PC board 14 is a battery 18 for providing power to sensor 12 when system power is unavailable. Extending from the bottom of sensor 12 is a base 20 having under-cut 22 which internally houses a sensor filter 28 (FIG. 3). Filter 28 is commonly used in the relevant art for preventing particles carried in the gaseous emissions to be tested from entering the sensor and, in addition, it prevents the liquid chemicals within the sensor from leaking out.

FIG. 3 shows a view of sensor 12 in the direction of arrows 3 of FIG. 1. The diameter of base 20 is approximately half that of sensor 12. Lying between and concentric to inner and outer diameters, 30 and 32, of base 20 is a rubber o-ring 34. O-ring 34 is slightly raised beyond surface 36 (FIG. 1) when sensor 12 stands alone not mated with a manifold block.

Referring again to FIG. 1, there is shown manifold block 40 having an emission gas intake channel 42 which allows gas to flow in the direction of arrow 44 due to a slightly positive air pressure within intake channel 42. At right angles to intake channel 42 is a chamber 46 which provides a pathway for the gas sampled to enter inlet 26. Also at right angles to intake channel 42 and across from chamber 46 is a gas outlet 48 to allow the sampled gas to exit manifold block 40. Outlet 48 has a threaded bore for mating with an outlet nozzle or valve (not pictured) for appropriately directing the sampled gas. For manufacturing purposes, intake channel 42 is bore-through the entire length of manifold block 40. A plug 51 is thereafter inserted at the end of intake channel 42 for the sole purpose of sealing off end 49 of manifold block 40.

As shown in FIG. 4, manifold block 40 also has a U-shaped slot 50 for mating with sensor 12. This is accomplished by first inserting sensor base 20 into slot 50 and then twisting or rotating the sensor assembly while forcibly sliding sensor base 20 in the direction of arrow 52 until in contact with the back wall 54 of slot 50. Mating slot 50 has dimension 50a such that o-ring 34 is compressed flush to gas sealing surface 36 when base 20 is fully engaged within slot 50, making for an air-tight seal.

The slidable sealing scheme of the present invention, in contrast to a screw-in mating scheme, allows a card-edge type connector to be employed. In this invention, the sensor can be rotated about its vertical axis to optimally position the card-edge connector 16 to optimally align with its corresponding plug (not shown). A card-edge connector and plug cannot be used with the screw-in sealing schemes of the prior art because of the inconsistent and unpredictable fitting tolerances between the threads of the sensor and manifold block. For example, a screw-in sensor subassembly, having a card-edge board connector, which optimally mates with a corresponding manifold block, by means of rotating about the z-axis, at a positive 45 degree angle from the x-axis of rotation, will only also be optimally positioned for purposes of connecting its card-edge connector with a corresponding plug if the card-edge connector is accessible to its plug at that exact same angle. With the present invention, however, such mating tolerances are irrelevant since card-edge connector 16 can be accurately aligned with a corresponding plug by rotating sensor base 20 within slot 50 until connector 16 is at the optimal angle.

The slidable mating scheme of the present invention is also advantageous in that it is fool proof and does not require tools for installation and removal of a sensor assembly. Furthermore, its performance does not depend upon variables, such as the amount of torque applied during installation, which are inherently related to threaded mating schemes.

Various modifications to the present invention will become apparent to those skilled in the art from the foregoing description and accompanying drawings. Hence, the present invention is to be limited solely by the scope of the following claims.

We claim:

1. A gas sensor comprising:

gas sensing means having a body with generally circular base, said base having a gas inlet;

a gas source manifold block with receiving means dimensioned to fit said base, said base being at least partially rotatable about its axis within said manifold block, said receiving means having an aperture in communication with said gas inlet and said manifold block for the passage of gases therebetween;

sealing means providing an airtight passage between said manifold block and said gas inlet;

a card edge connector mounted on said body and extending generally in a direction transverse to the axis of said body, said connector having a self-contained power source mounted therewith to said body; and a mating socket for transmitting data to a gas monitor, said card edge connector alignable with and connectable to said mating socket when said base is rotated in said slot.

2. A sensor support subassembly for use in testing gases, comprising:

a sensor unit having a generally cylindrical base and a gas inlet means in said base;

a manifold block having a gas channel for the passage of gases, said block having a slot therein dimensioned to receive said base, said base being at least partially rotatable about its axis in said slot, said block also having a chamber proximate to and in communication with said channel for the passage of gases therebetween, said slot having an aperture in communication with said chamber and in registration with said gas inlet means for the passage of gases from said channel through said chamber and said aperture to said gas inlet means;

sealing means such that when said aperture and said gas inlet means are in registration with one another, an air-tight passage is created between said gas inlet means and said chamber;

a card edge connector having a self-contained power source mounted therewith to said sensor unit, said card edge connector mounted on said sensor unit and extending in a direction generally transverse to the axis of said cylindrical base; and a mating socket for transmitting data to a gas monitor, said card edge connector alignable with and connectable to said mating socket when said base is rotated in said slot.

* * * * *